United States Patent [19]
Hagemann

[11] 3,956,468
[45] May 11, 1976

[54] PROCESS FOR THE PREPARATION OF CARBONYLDIISOCYANATE

[75] Inventor: Hermann Hagemann, Cologne, Germany

[73] Assignee: Bayer Aktiengesellschaft, Leverkusen, Germany

[22] Filed: Feb. 11, 1975

[21] Appl. No.: 548,933

[30] Foreign Application Priority Data
Feb. 20, 1974 Germany............................ 2408069

[52] U.S. Cl................................ 423/365; 423/416
[51] Int. Cl.²........................................... C01C 3/00
[58] Field of Search ............ 423/365, 364, 371, 416

[56] References Cited
OTHER PUBLICATIONS

German Printed Appplication No. 1,266,288 at Nachbaur, published Apr. 18, 1968, 2 pps. spec., 1 sht. drwg.

Primary Examiner—Earl C. Thomas
Attorney, Agent, or Firm—Joseph C. Gil; Gene Harsh

[57] ABSTRACT

The instant invention is directed to a process for preparing carbonyldiisocyanate comprising reacting N-chlorocarbonylisocyanate with trichloroisocyanuric acid and/or an alkali metal salt of dichloroisocyanuric acid at a temperature of from about 20°C to about 200°C.

6 Claims, No Drawings

PROCESS FOR THE PREPARATION OF CARBONYLDIISOCYANATE

BACKGROUND OF THE INVENTION

It is known that compounds which contain positively-polarized chlorine atoms, such as N-chloro compounds, and compounds which contain negatively-polarized chlorine atoms, such as acid chlorides may be reacted together with elimination of chlorine. These reactions generally require high temperatures or even the use of equimolar amounts of Friedel-Crafts catalysts.

One process known in the art, for example, describes the formation of trichloroacetylisocyanate from trichloroacetyl chloride and trichloroisocyanuric acid at a temperature of from 160° to 170°C, (see Zh. Org. Khim. 9 (1973) 1815–18).

It is also known (DAS No. 1,266,288), that carbonyldiisocyanate may be prepared by the thermolysis of N-trichloroisocyanuric acid at a temperature of from 200° to 400°C with simulataneous formation of $NCl_3$, in accordance with the following equation:

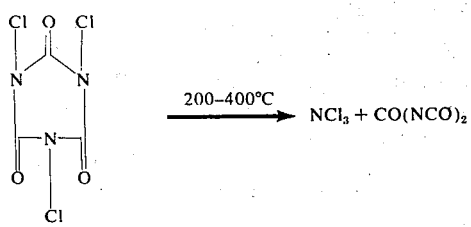

This reaction is accompanied by said reactions and is difficult to control because of the simultaneous formation of the highly explosive compound, $NCl_3$.

Another process for preparing $CO(NCO)_2$ is the reaction of difluorophosgene with potassium cyanate in a LiCl/KCl melt at temperatures of about 400°C. This method of preparation involves relatively high technical expenditure because of the low conversion rates obtained and because of high reaction temperatures required, (see Angew. Chem. 79, 860 (1967).

DESCRIPTION OF THE INVENTION

It has now surprisingly been found that a mixture of Cl-CO-NCO with trichloroisocyanuric acid and/or an alkali metal salt of dichloroisocyanuric acid may be converted almost quantitatively into $CO(NCO)_2$ with elimination of chlorine, the reaction proceeds even at temperatures as low as 30° to 40°C and proceeds very vigorously at about 60° to 70°C. The reaction is preferably conducted in an inert oganic solvent, such as trichlorobenzene or o-dichlorobenzene.

Accordingly, the present invention relates to a process for the preparation of carbonyldiisocyanate which is characterized in that trichloroisocyanuric acid and/or an alkali metal salt of dichloroisocyanuric acid is reacted with N-chlorocarbonyl isocyanate at a temperature of from about 20° to about 200°C.

The process according to the invention may be represented by the following equation:

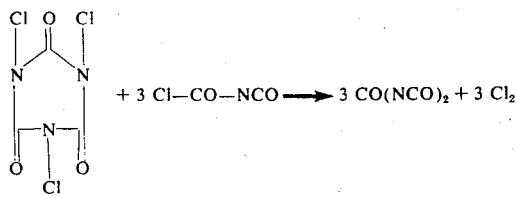

Instead of trichloroisocyanuric acid, an alkali metal salt of dichloroisocyanuric acid may be used in the process according to the invention. It is preferred to use the sodium or potassium salt of dichloroisocyanuric acid. When such salts are used, it is advisable to increase the concentration of the isocyanuric acid derivative because the above reaction takes place between the positively-polarized chlorine atom of the isocyanuric acid derivative and the negatively-polarized chlorine atom of the chlorocarbonylisocyanate with formation of $Cl_2$.

For ease of separation of the product, it has been found preferable to carry out the reaction in a solvent which has a boiling point substantially above 104°C, (i.e., the boiling point of $CO(NCO)_2$), and which is substantially inert towards chlorine under the reaction conditions. The reaction may, of course, also be carried out in a lower boiling solvent, in a solvent which binds chlorine chemically or, in a solventfree system.

The temperature may be varied within wide limits but the reaction is preferably carried out at temperatures below about 200°C in order to ensure that no $NCl_3$ will be formed. The reaction will even proceed at room temperature, so that a temperature range of from about 20° to about 200°C may be quoted. It is preferred to employ temperatures of from about 40° to about 150°C and temperatures of from about 60° to about 80°C are most preferred.

The above-mentioned isocyanuric acid derivative can generally be introduced into the reaction vessel in the form of a suspension in a solvent and the N-chlorocarbonylisocyanate would then be slowly added thereto. Alternatively, the isocyanurate acid derivative may be added to the ClCONCO.

The use of equivalent quantities, i.e. 1 mol trichloroisocyanuric acid per 3 mols chlorocarbonylisocyanate or 1 mol of an alkali metal salt of dichloroisocyanuric acid per 2 mols chlorocarbonylisocyanate, results in yields of over 80%, (based on chlorocarbonylisocyanate). If desired, one of the reactants may, of course, be used in excess so that the component used in excess may be recovered after the reaction. In order to approach quantitative conversion of the isocyanuric acid derivative, it is sometimes advisable to use an excess of chlorocarbonylisocyanate above the given proportions since excess chlorocarbonylisocyanate may easily be removed from the final product by distillation.

Carbonyldiisocyanate is an extremely reactive diisocyanate. For example, even at room temperature it reacts with the slightest traces of moisture present in any inert solvent present. It is therefore an ideal dehydrating agent for producing absolute solvents. Carbonyldiisocyanate differs advantageously from known dehydrating agents, for example those used for preparing absolute ether (metallic sodium or phosphorus pentoxide), in that it is miscible in any proportions with the solvent which is to be dehydrated. One disadvantage of known dehydrating agents is that their active surface to a large extent becomes inactivated by the sodium hydroxide formed or by a so-called "skin" of polyphosphoric acid so that the dehydrating agent must be continuously renewed. Such disadvantage is completely obviated when using the product of this process as a dehydrating agent. For example, in preparing absolute ether, all that is required is to add a suitable quantity of carbonyldiisocyanate to ether which has been pre-dried, for example over calcium chloride. The mixture is then kept at room temperature for a few minutes and the ether is subsequently recovered, such as by distillation.

Although carbonyldiisocyanate is not a novel compound, it may be said that the process according to the invention has for the first time enabled this substance to be prepared by a technically simple and economic method.

EXAMPLE 1

232.5 g (1 mol) trichloroisocyanuric acid, suspended in 750 ml o-dichlorobenzene, are introduced into a reaction vessel and 317.5 g (3 mol) N-chlorocarbonylisocyanate are added at a temperature of 100°C over a period of 4 hours. Vigorous evolution of chlorine takes place during the whole time of this addition. Stirring is then continued at 150°C for an extra minute and the reaction mixture is then distilled over a 20 cm packed column. 276 g, (82% of the theoretical amount), of carbonyldiisocyanate is obtained as a water-clear liquid, (b.p.: 104°C).

EXAMPLE 2

317.5 g (3 mol) N-chlorocarbonylisocyanate in 500 ml o-dichlorobenzene are introduced into a reaction vessel and 232.5 g (1 mol) trichloroisocyanuric acid are added portionwise in solid form by means of a powder feed funnel at a temperature of from 60° to 70°C over a period of about 4 hours. Vigorous evolution of chlorine takes place as in Example 1 and 290 g, (86% of the theoretical amount), of $CO(NCO)_2$ are obtained after distillation.

EXAMPLE 3

220 g (1 mol) monosodium dichloroisocyanuric acid, suspended in 750 ml o-dichlorobenzene, are introduced into a reaction vessel and 520 g (4.92 mol) ClCONCO are added at a temperature of from 100° to 120°C. After removal of excess ClCONCO by distillation, 210 g, (93.5% of the theoretical amount, based on positively-polarized chlorine) of $CO(NCO)_2$, (b.p.: 104°C), are obtained.

EXAMPLE 4

About 10 g carbonyldiisocyanate are added, at 20°C to 1 liter of diethylether which has been pre-dried over calcium chloride. The mixture is kept at room temperature for ½ hour. The ether is then recovered in the pure form by simple distillation in a carefully dried distillation apparatus. Metallic sodium is then forced into this dehydrated ether with a sodium press. The metal surface of the sodium wire remains practically unchanged in its metallic appearance for 24 hours.

What is claimd is:

1. A process for the preparation of carbonyldiisocyanate comprising reacting trichloroisocyanuric acid and/or an alkali metal salt of dichloroisocyanuric acid with N-chlorocarbonylisocyanate at a temperature of from about 20°C to about 200°C.

2. The process of claim 1, wherein the reaction is conducted in the presence of an organic solvent.

3. The process of claim 2, wherein said organic solvent has a boiling point of above 104°C.

4. The process of claim 3, wherein said solvent is o-dichlorobenzene.

5. The process of claim 1, wherein the reaction is conducted at a temperature of from bout 40° to about 150°C.

6. The process of claim 5, wherein the reaction is conducted at a temperature of from about 60° to about 80°C.

* * * * *